United States Patent [19]
Gjerde et al.

[11] Patent Number: 6,027,898
[45] Date of Patent: Feb. 22, 2000

[54] CHROMATOGRAPHIC METHOD FOR MUTATION DETECTION USING MUTATION SITE SPECIFICALLY ACTING ENZYMES AND CHEMICALS

[75] Inventors: Douglas T. Gjerde, Saratoga; Paul D. Taylor, Palo Alto, both of Calif.

[73] Assignee: Transgenomic, Inc., San Jose, Calif.

[21] Appl. No.: 09/136,084

[22] Filed: Aug. 18, 1998

Related U.S. Application Data

[60] Provisional application No. 60/055,676, Aug. 18, 1997, and provisional application No. 60/062,413, Oct. 14, 1997.

[51] Int. Cl.[7] ........................................... C12Q 1/68
[52] U.S. Cl. ..................... 435/6; 436/501; 536/25.3; 536/25.4
[58] Field of Search ................. 435/6; 436/501; 536/25.3, 25.4

[56] References Cited

U.S. PATENT DOCUMENTS

| | | | |
|---|---|---|---|
| 4,395,486 | 7/1983 | Wilson et al. | 435/6 |
| 4,656,127 | 4/1987 | Mundy | 435/6 |
| 4,683,202 | 7/1987 | Mullis | 435/91 |
| 5,175,273 | 12/1992 | Bischofberger et al. | 536/27 |
| 5,217,863 | 6/1993 | Cotton et al. | 435/6 |
| 5,376,526 | 12/1994 | Brown et al. | 435/6 |
| 5,459,039 | 10/1995 | Modrich et al. | 435/6 |
| 5,556,750 | 9/1996 | Modrich et al. | 435/6 |
| 5,585,236 | 12/1996 | Bonn et al. | 435/5 |
| 5,589,329 | 12/1996 | Winkler et al. | 435/5 |
| 5,698,400 | 12/1997 | Cotton et al. | 435/6 |
| 5,763,178 | 6/1998 | Chirikjian et al. | 435/6 |

FOREIGN PATENT DOCUMENTS

| | | | |
|---|---|---|---|
| 95/29258 | 11/1995 | WIPO | C12Q 1/68 |
| 97/09422 | 3/1997 | WIPO | C12N 9/22 |
| WO 97/21837 | 7/1997 | WIPO | C12Q 1/68 |

OTHER PUBLICATIONS

Brow et al, Cleavase Gragment Length Polymorphism Analysis for Mutation Scanning, Biomedical Products (Sep. 1997).

Chan et al. Sequence Specifity and Biochemical Characterization fo He Rusa Holliday Junction reolvase of Excherichia coli, The Journal of Biological Chemistry, vol. 272, No. 23, Jun. 6, 1997 pp. 14873–14882.

Cotton et al, Reactivity of Cytosine Ans Thymine in Single–Base–Pair Mismatches With Hydrozylamine an Osmium Tetroxide and its Application to the Stury of Mutations, Proc. Natl. Acad. Sci. USA, 85:4397–4401 (Jun. 1988).

Cotton et al, Slowly by Surely Towards Better Scanning for Mutations, TIG, vol. 13 No. 2: 43–46 (Feb. 1997).

Ellis et al, Chemical Cleavage of Mismatch: A New Look at an Established Method, Human Mutation, 11: 345–353 (1998).

Gidney et al. 1.10–Phenanthroline and 2,2–Bipyridyl Complexes of Rhodium (iii), JCS Dalton (1972) pp. 2621–2628.

Giraud–Panis et al. T4 Endonuclese VII, Importance of a Histidine–Asparate Cluster Within the Zinc–Binding Domain, The Journal of Biological Chemistry, 271, pp. 33148–33155, 1996.

(List continued on next page.)

*Primary Examiner*—Ardin H. Marschel
*Attorney, Agent, or Firm*—William B. Walker

[57] ABSTRACT

A method for analyzing a sample of double stranded DNA to determine the presence of a mutation therein comprises contacting the sample with a mutation site binding reagent, and chromatographically separating and detecting the product. The chromatographic separation can be performed using Matched Ion Polynucleotide Chromatography, size exclusion chromatography, ion exchange chromatography, or reverse phase chromatography. The mutation site binding reagent can be an enzyme or a non-proteinaceous chemical reagent. In one embodiment, a mutation site binding reagent binds to the site of mutation and alters the chromatographic retention time. In another embodiment, a mutation site binding reagent cleaves at the site of mutation, resulting in an increase in the number of fragments.

31 Claims, 2 Drawing Sheets

OTHER PUBLICATIONS

Holmlin et al., RU(PHEN)2DPPZ2+ Luminescence: Dependence on DNA Sequences and Groove–Binding Agents, Inorg. Chem. (1998)37:29–34.

http://journals.wiley.co . . . 9–7794/abs/v7n3p256.html (Jun. 26, 1998) Citing: Hansen et al, Human Mutation, Vol. 7 No. 3: 256–263 (1996).

hhtp://wsrv.clas.virginia.edu/~rjh9u/restdna1.html Restriction Enzyme Cleavage of DNA, (Jun. 26, 1998).

http://www.jbc.org/cgi/c . . . =QID_NOT_SET&FIRSTINDEX=(Sep. 21, 1998) Citing: J. Biol. Chem., vol. 273 Iss 15: 9202–9207 (Apr. 1998).

http://www.jbc.org/cgi/c . . . =QID_NOT_SET&FIRSTINDEX=(Sep. 21, 1998) Citing: Taylor et al, Strand Specificity of Nicking of DNA and CHI Sites by RECBCD Ezyme, JBC Online, vol. 270 No. 41: 24459–24467 (Oct. 1995).

Huber et al, High–Resolution Liquid Chromatography of Oligonucleotides on Nonporous Alkylated Styrene–Divinylbenzene Copolymers, Analytical Biochemistry, 212: 351–358 (1993).

Jackson et al, Recognition of DNA Base Mismatches by a Phodium Intercalator, J. Am. Chem. Soc., vol. 119 No. 32: 12986–12987 (1997).

Marshal et al, Detection of Mutations by Cleavage of DNA Heteroduplexes with Bacteriophage Resolvases, Nature Genetics, 9: 177–183 (Feb. 1995).

Marshal et al, Practical Methods of Mutation Detection, Genetics & Development, 6: 275–280 (1998).

Molecular CLoning, A Laboratory Manual, 2nd ed, Cold Spring Harbor Laboratory Press, 1989, pp. 13.2–13.10.

Myers et al, Detection of Single Base Changes in DNA: Ribonuclease Cleavage and Denaturing Gradient Gel Electrophoresis, Genomic Analysis: A Practical Approach, PRL Press, K. Davies, ed. (1988).

Myers et al. Genomic Analysis: A Practical Approach, IRL Press, K. Davis, ed. (1988) pp. 95–158.

Oleykowski et al, Mutation Detection Using a Novel Plant Endonuclease, Nucleic Acids Research, vol. 26 No. 20: 4597–4602 (1998).

Rowley et al., Ultrarapid Mutation Detection by Multiplex, Solid–Phase Chemical Cleavage, Genomics, 30, 574–582, 1995.

Shida et al. Anlysis of Substrate Specificity of the RUVC Holliday Junction Resolvase with Syntheic Holliday Junctions, The Journal of Biological Chemistry, vol. 271, No. 42, Oct. 18, 1996, pp. 26105–26109.

Smith et al. Mutation Detection with MUTH, MUTL, and MUTS Mismatch Repair Proteins, Proc. Natl. Acad. Sci. USA, Genetics, 93, pp. 4374–4379, Apr. 1996.

Stemp et al, Oxidation of Guanine in DNA by Ru(phen)2(dppz)3+ Using the Flash–Quench Technique, J. Am. Chem. Soc., vol. 119 No. 12:2921–2923 (1997).

Taylor, Graham R., Laboratory Methods for the Detection of Mutations and Polymorphisms in DNA, Ch. 9, 18–22, CRC Press, Boca Raton, New York (1997).

Wagner et al. Mutation Detection Using Immobilized Mismatch Binding Protein (MUTS), Nucleic Acids Research, 25, 19, pp. 3944–3948, 1995.

Xu et al. Determining the Site and Nature of DNA Mutations with the Cloned MUTY Mismatch repair Enzyme, Carcinogenesis, vol. 17, No. 2, pp. 321–326, 1996.

Youil et al, Screening for Mutations by Enzyme Mismatch Cleavage with T4 Endonuclease VII, Proc. Natl. Acad. Sci. USA, 92: 87–91 (1995).

Sitlani et al DNA Photocleavage by Phenanthrenequinon Diimine Complexes of Phodium (III): Shape–Selective Recognition and Reaction, J. Am. Chem. Soc. 1992, 114, 2303–2312.

CHROMATOGRAPHIC METHOD FOR MUTATION DETECTION USING MUTATION SITE SPECIFICALLY ACTING ENZYMES AND CHEMICALS

CROSS REFERENCE TO RELATED CO-PENDING APPLICATION

This application is a regular U.S. patent application under 35 U.S.C. §111 (a) and 35 U.S.C. §1.53 (b) and claims priority under 35 U.S.C. §111 (b). from the following co-pending, commonly assigned provisional applications No. 60/055,676 filed Aug. 18, 1997, and No. 60/062,413 filed Oct. 14, 1997.

FIELD OF THE INVENTION

The present invention concerns an improved chromatographic method for detection of mutations in nucleic acids.

BACKGROUND OF THE INVENTION

The ability to detect mutations in double stranded polynucleotides, and especially in DNA fragments, is of great importance in medicine, as well as in the physical and social sciences. The Human Genome Project is providing an enormous amount of genetic information which is setting new criteria for evaluating the links between mutations and human disorders (Guyer, et al., *Proc. Natl. Acad. Sci. USA* 92:10841 (1995)). The ultimate source of many diseases, for example, is described by genetic code that differs from wild type (Cotton, TIG 13:43 (1997)). Understanding the genetic basis of disease can be the starting point for a cure. Similarly, determination of differences in genetic code can provide powerful and perhaps definitive insights into the study of evolution and populations (Cooper, et. al., *Human Genetics* vol. 69:201 (1985)). Understanding these and other issues related to genetic coding is based on the ability to identify anomalies, i.e., mutations, in a DNA fragment relative to the wild type. A need exists, therefore, for a methodology to detect mutations in an accurate, reproducible and reliable manner.

DNA molecules are polymers comprising sub-units called deoxynucleotides. The four deoxynucleotides found in DNA comprise a common cyclic sugar, deoxyribose, which is covalently bonded to any of the four bases, adenine (a purine), guanine (a purine), cytosine (a pyrimidine), and thymine (a pyrimidine), hereinbelow referred to as A, G, C, and T respectively. A phosphate group links a 3'-hydroxyl of one deoxynucleotide with the 5'-hydroxyl of another deoxynucleotide to form a polymeric chain. In double stranded DNA, two strands are held together in a helical structure by hydrogen bonds between, what are called, complimentary bases. The complimentarity of bases is determined by their chemical structures. In double stranded DNA, each A pairs with a T and each G pairs with a C, i.e., a purine pairs with a pyrimidine. Ideally, DNA is replicated in exact copies by DNA polymerases during cell division in the human body or in other living organisms. DNA strands can also be replicated in vitro by means of the Polymerase Chain Reaction (PCR).

Sometimes, exact replication fails and an incorrect base pairing occurs, which after further replication of the new strand results in double stranded DNA offspring containing a heritable difference in the base sequence from that of the parent. Such heritable changes in base pair sequence are called mutations.

In the present invention, double stranded DNA is referred to as a duplex. When the base sequence of one strand is entirely complimentary to base sequence of the other strand, the duplex is called a homoduplex. When a duplex contains at least one base pair which is not complimentary, the duplex is called a heteroduplex. A heteroduplex can be formed during DNA replication when an error is made by a DNA polymerase enzyme and a non-complimentary base is added to a polynucleotide chain being replicated. Chemical damage, UV damage, and ionizing radiation can also cause lesions, which are usually repaired. Repair of the heteroduplex is usually rapid, but it may be the original sequence that is repaired to match the erroneous base. Errors in the repair may lead to mutations. Further replications of a heteroduplex will, ideally, produce homoduplexes which are heterozygous, i.e., these homoduplexes will have an altered sequence compared to the original parent DNA strand. When the parent DNA has a sequence which predominates in a naturally occurring population, it is generally called "wild type."

Many different types of DNA mutations are known. Examples of DNA mutations include, but are not limited to, "point mutation" or "single base pair mutations" wherein an incorrect base pairing occurs. The most common point mutations comprise "transitions" wherein one purine or pyrimidine base is replaced for another and "transversions" wherein a purine is substituted for a pyrimidine (and visa versa). Point mutations also comprise mutations wherein a base is added or deleted from a DNA chain. Such "insertions" or "deletions" are also known as "frameshift mutations". Mutations affecting multiple base pairs can also occur and may be important, although they occur with less frequency than point mutations. A more detailed discussion of mutations can be found in U.S. Pat. No. 5,459,039 to Modrich (1995), and U.S. Pat. No. 5,698,400 to Cotton (1997). These references and the references contained therein are incorporated in their entireties herein.

The sequence of base pairs in DNA code for the production of proteins. In particular, a DNA sequence in the exon portion of a DNA chain codes for the a corresponding amino acid sequence in a protein. Therefore, a mutation in a DNA sequence may result in an alteration in the amino acid sequence of a protein. Such an alteration in the amino acid sequence may be completely benign or may inactivate a protein or alter its function to be life threatening or fatal. On the other hand, mutations in an intron portion of a DNA chain would not be expected to have a biological effect since an intron section does not contain code for protein production. Nevertheless, mutation detection in an intron section may be important, e.g., in studying regulation of gene expression, or in forensic investigations.

Detection of mutations is, therefore, of great interest and importance in diagnosing diseases, understanding the origins of disease and the development of potential treatments. Detection of mutations and identification of similarities or differences in DNA samples is also of critical importance in increasing the world food supply by developing diseases resistant and/or higher yielding crop strains, in forensic science, in the study of evolution and populations, and in scientific research in general (Guyer, et al., *Proc. Natl. Acad. Sci. USA* 92:10841 (1995); Cotton, TIG 13:43 (1997)).

Alterations in a DNA sequence which are benign or have no negative consequences are sometimes called "polymorphisms". In the present invention, any alterations in the DNA sequence, whether they have negative consequences or not, are called "mutations". It is to be understood that the method of this invention has the capability to detect mutations regardless of biological effect or lack thereof. For the sake of simplicity, the term "mutation" will be used throughout to mean an alteration in the base sequence of a DNA strand compared to a reference strand. It is to be understood that in the context of this invention, the term "mutation" includes the term "polymorphism" or any other similar or equivalent term of art.

Analysis of DNA samples has historically been done using gel electrophoresis. Capillary electrophoresis has also been used to separate and analyze mixtures of DNA.

Gel based techniques are operationally difficult to implement and require highly skilled personnel. In addition, the analyses are lengthy and require a great deal of set up time. A denaturing capillary gel electrophoresis analysis of a 90 base pair fragment takes more than 30 minutes and a denaturing gel electrophoresis analysis may take 5 hours or more. The long analysis time of the gel methodology is further exacerbated by the fact that the movement of DNA fragments in a gel is inversely proportional, in a geometric relationship, to their length. Therefore, the analysis time of longer DNA fragments can be often be untenable.

In addition to the deficiencies of denaturing gel methods mentioned above, these techniques are not always reproducible or accurate since the preparation of a gel and running an analysis can be highly variable from one operator to another.

An entirely different approach to mutation detection is based on the well known fact that certain enzymes can recognize deviations in base pair sequence in a DNA double strand. This recognition of the presence of a mutation can take two forms. The enzyme will either cleave a DNA double strand at or near the mutation site, or bind to the DNA double strand at the site of a base pair mismatch.

Enzyme based mutation detection assays have also relied on gel based analytical techniques to determine the presence or absence of a mutation. In addition to the limitations related to gel based analytical methods already discussed hereinabove, the sensitivity of gel based methods is relatively low compared to MIPC. Therefore, when gel electrophoresis is used to analyze a sample for the presence of a mutation, the sample must be allowed to remain in contact with the enzyme for an extended time in order to allow the maximum build-up of product strands. However, extended contact with enzymes can result in non-specific cleavage, which creates ambiguity in the analytical result.

SUMMARY OF THE INVENTION

It is an object of the invention to provide an improved analytical method for the detection of mutations.

It is an additional object of the invention to provide a method for mutation detection which is highly reproducible, accurate, easily implemented and which can be automated for use with high throughput mutation detection assays or other analyses which require screening a large number of samples.

Therefore, in one aspect, the invention provides a method for analyzing a sample of double stranded DNA to determine the presence of a mutation in the DNA sample. The method comprises, (a) contacting said sample with a mutation site binding reagent, and (b) chromatographically separating and detecting the product of step (a). The method further comprises a step comparing the separated product of step (b) to a standard.

The chromatographic step can be performed by Matched Ion Polynucleotide Chromatography, size exclusion chromatography, ion exchange chromatography, or reverse phase chromatography. The DNA sample can be hybridized with corresponding wild type DNA prior to step (a).

In one embodiment, the mutation site binding reagent is a protein reagent which binds within the vicinity of said mutation site. The protein reagent is selected from the group consisting of endonucleases, restriction enzymes, ribonucleases, mismatch repair enzymes, resolvases, helicases, ligases, and antibodies specific for mismatches. The protein reagent can be modified by site specific mutagenesis. In a preferred embodiment, the protein reagent cleaves at least one strand of the DNA sample within the vicinity of said mutation site.

In another embodiment of the invention, the mutation site binding reagent is a non-proteinaceous chemical reagent which binds or cleaves within the vicinity of the mutation. Such reagents include intercalators. Specific examples include the class of organometallic DNA intercalators which recognize base pair sequences and which intercalate within the vicinity of a mutation site. Specific examples of such compounds contain rhodium or ruthenium and include bis (2,2'-bipyridyl)chrysenequinone diimine rhodium(III), bis (2,2'-bipyridyl)chrysenequinone diimine rhodium(III), (2,2'-bipyridyl)-bis(phenanthrenequinone) diimine rhodium(III), (bis(phenanthroline)dipyridophenazine ruthenium(II), bis (phenanthroline)dipyridophenazine ruthenium(III). In a further embodiment of the invention, exposure of a DNA/intercalator complex to light of an appropriate wave length causes the DNA strand to cleave at or near the binding site.

In another aspect, the invention provides a chromatographic method for analyzing a DNA sample to determine the presence of mutations in the DNA sample, the method comprising, (a) separating the DNA sample using a chromatographic method which produces a first chromatogram comprising peaks or other shapes which represent separated components of the sample; (b) contacting said DNA sample with a mutation site binding reagent; (c) separating the product of step (b) by the chromatographic method of step (a) to produce a second chromatogram. The method further comprises comparing the chromatogram of step (c) to the chromatogram of step (a), wherein a change in the retention time or the number of peaks or other shapes in the chromatogram of step (c) indicates the presence of a mutation in said sample.

The chromatographic method can be selected from the group consisting of size exclusion chromatography, ion exchange chromatography, and reverse phase chromatography. The preferred chromatographic method of the invention is Matched Ion Polynucleotide Chromatography (MIPC).

In a preferred embodiment, the DNA sample is hybridized with corresponding wild type prior to initiating the analysis.

The mutation site binding reagent can be an enzyme or a non-proteinaceous chemical reagent. Examples of a chemical reagent include organometallic DNA intercalators containing rhodium or ruthenium. Such intercalators comprise bis(2,2'-bipyridyl)chrysenequinone diimine rhodium(III).

When a chemical reagent recognizes a mutation site, the chemical reagent binds at or near the mutation site. The sample is thus altered if it contains a mutation. An altered form of the sample can be separated and detected by MIPC.

When an enzyme recognizes a sequence variation in a DNA sample, the enzyme cleaves a DNA duplex at or near a mutation site or nicks a single strand of a DNA duplex at or near a site of base pair mismatch in a heteroduplex. The enzyme can also bind at or near a mutation. The sample is thus altered if it contains a mutation. An altered form of the sample can be separated and detected by MIPC.

Enzymes which can be used in the present invention include endonucleases, restriction enzymes, ribonucleases, mismatch repair enzymes, resolvases, helicases, ligases, and antibodies specific for mismatches. More specifically, the enzyme can be selected from the group consisting of T4 endonuclease 7, T7 endonuclease 1, S1, mung bean endonuclease, MutY, MutS, MutH, MutL, cleavase, and HINF1.

DETAILED DESCRIPTION OF THE INVENTION

In its most general form, the present invention relates to an improved method of mutation detection in which chromatography is used to separate and detect DNA fragments of samples which have been contacted with enzymes or chemical reagents. More specifically, the invention relates to an improved mutation detection method which depends on the size based MIPC separation and detection of DNA fragments in samples which have been contacted with enzymes or chemical reagents which can recognize mutations by cleaving or binding to the DNA at or near the mutation site. As will be discussed more fully hereinbelow, the method of the invention can also be used to detect mutations by contacting a sample with an enzyme, e.g., a restriction enzyme, which does not cleave a DNA sample containing a mutation but only cleaves wild type.

Recently, a chromatographic method called Matched Ion Polynucleotide Chromatography (MIPC) was introduced to effectively separate mixtures of double stranded polynucleotides, in general and DNA, in particular, wherein the separations are based on base pair length (U.S. Pat. No. 5,585,236 to Bonn (1996); Huber, et al., *Chromatographia* 37:653 (1993); Huber, et al., *Anal. Biochem.* 212:351 (1993)). These references and the references contained therein are incorporated herein in their entireties. MIPC is not limited by any of the deficiencies associated with gel based separation methods.

The term "Matched Ion Polynucleotide Chromatography" as used herein is defined as a process for separating single and double stranded polynucleotides using non-polar separation media, wherein the process uses a counter-ion agent, and an organic solvent to release the polynucleotides from the separation media. MIPC separations can be completed in less than 10 minutes, and frequently in less than 5 minutes. MIPC systems (WAVE™ DNA Fragment Analysis System, Transgenomic, Inc. San Jose, Calif.) are equipped with computer controlled ovens which enclose the columns and fluid areas.

MIPC uses unique non-polar separation media which include organic polymers, silica media having a non-polar surface comprising coated or covalently bound organic polymers or covalently bound alkyl and/or aryl groups, continuous monolith or rod columns comprising non-polar silica gel or organic polymer. The separation media used in MIPC can be porous or non-porous. A detailed description of the MIPC separation process, MIPC separation media, and MIPC systems is found in U.S. Pat. No. 5,772,889 (1998) to Gjerde and in co-pending U.S. patent applications Ser. Nos. 09/058,580 filed Apr. 10, 1998; Ser. No. 09/058,337 filed Apr. 10, 1998; Ser. No. 09/065,913 filed Apr. 24, 1998; Ser. No. 09/081,040 filed May 18, 1998; Ser. No. 09/081,039 filed May 18, 1998; Ser. No. 09/080,547 filed May 18, 1998, and U.S. patent application Ser. No. 09/129,105 entitled "Improved Mutation Detection Method" filed Aug. 4, 1998. The entire contents of this patent and these applications are hereby incorporated by reference. MIPC systems and separation media are commercially available (Transgenomic, Inc. San Jose, Calif.). The entire MIPC analysis can be automated by means of a desk top computer and a sample auto-injector. Analytical data for each sample can be analyzed in real time, or collected and stored in a computer memory device for analysis at a later time.

The term "mutation" is often used to denote a DNA sequence variation from wild type which produces harmful effects in an organism. The term "polymorphism" is often used to denote a sequence variation in DNA which is benign. In the present invention, it is to be understood that the term "mutation" refers to any DNA fragment which has a base sequence which varies from the wild type and includes "polymorphisms". "Mutations" in the present invention include all mutations, including those which have been produced in in vitro processes, such as PCR.

Non-limiting examples of how mutations occur in DNA, i.e., variations in base pair sequence relative to wild type, include errors made during DNA replication in which a non-complimentary base is added to a DNA template, a base is deleted, or a base is inserted. A more detailed discussion of mutations can be found in U.S. Pat. No. 5,459,039 to Modrich (1995), and U.S. Pat. No. 5,698,400 to Cotton (1997). These references and the references contained therein are incorporated in their entireties herein. All types of mutations can be detected by the methods of the present invention.

One embodiment the present invention provides an improved chromatographic method for analyzing DNA samples for the presence of one or more mutations therein. The method comprises contacting a DNA sample with a mutation site binding reagent for recognizing a mutation site to produce a product. The product can be a cleavage product or can be a complex consisting of mutation binding site binding reagent bound to the DNA. The product is chromatographed to separate and detect the components therein. The separated product is then compared to a standard. The standard is generally the DNA sample prior to contact with the mutation site binding reagent. A change in the retention time or the number peaks in the chromatogram of the sample after contact with the mutation site binding reagent compared to the standard, indicates the presence of, at least, one mutation site.

In one embodiment, the mutation site binding reagent is a protein reagent which binds in the vicinity of the mutation site. Examples include endonucleases, restriction enzymes, ribonucleases, mismatch repair enzymes, resolvases, helicases, ligases, and antibodies specific for mismatches. In addition to binding, the protein reagent can also cleave at least one strand of the sample in the vicinity of the mutation site. In a related embodiment, the sample is hybridized with corresponding wild type prior to being contacted with the mutation site binding reagent.

Although any chromatographic method, including MIPC, size exclusion chromatography, ion exchange chromatography, or reverse phase chromatography, can be used in the method of the present invention, the preferred chromatographic step comprises MIPC. Separations based on gel electrophoresis are excluded from the definition of chromatography as used herein.

An important aspect of the invention, surprisingly discovered by the Applicants, is that samples which have been treated with sequence recognition enzymes can be analyzed directly by MIPC or DMIPC. It is not necessary to remove any endogenous reagents or by-products prior to analysis. This is unusual, since such endogenous material, especially proteins, usually interfere in HPLC separations. This discovery makes possible the unattended, automated analysis of multiple samples in mutation detection screening assays.

In another embodiment, the method of the invention can also be practiced by employing a non-proteinaceous chemical reagent which binds in the vicinity of a mutation site. Such reagents include chemical intercalators which recognize a base sequence and are an effective means for detecting the presence of a mutation. Such compounds are exemplified by organometallic substances, generally containing rhodium or ruthenium. A specific, non-limiting example, of such a site recognition organometallic intercalator is bis(2,2'-bipyridyl)chrysenequinone diimine rhodium(III).

The chemical reagent can also cleave the sample in the vicinity of the mutation site when the intercalated DNA is exposed to light having a suitable wavelength. An example of such a wavelength is about 365 nm such as produced by a mercury/xenon arc lamp.

In another embodiment, the invention provides an improved chromatographic method for analyzing DNA samples for the presence of one or more mutations. The method comprises separating a DNA sample using a chromatographic method to produce a first chromatogram comprising peaks or other shapes which represent the separated components of the sample. The sample is then contacted with a mutation site binding reagent which recognizes a DNA base sequence to produce a product. Such a mutation site binding reagent can be an enzyme or chemical reagent which can recognize variations in a DNA sequence relative to wild type. Separating the product resulting from contacting the sample with the mutation site binding reagent by chromatography produces a second chromatogram. If there is a change in the number of peaks or their retention time in the second chromatogram compared to the first chromatogram, then the sample contains a mutation.

Any chromatographic method which can effect the separation of double stranded DNA fragments can be used in the mutation detection analysis of the invention, including size exclusion chromatography, ion exchange chromatography and reverse phase chromatography. However, the preferred method of the invention uses MIPC. Therefore the discussion to follow will focus on the use of MIPC to implement the method of the invention and refers to each of the embodiments described above.

Since MIPC separates DNA fragments on the basis of base pair length, ambiguity in the mutation detection analysis is eliminated when comparing chromatograms of samples prior to, and post contact with enzymes or chemical reagents which are specific for mutation sites, or for the mis-matched bases resulting from hybridization. Any changes observed in the number of peaks must represent cleaved, shorter fragments. If the prior to, and post contact chromatograms show the same number of peaks, but having different retention times, then the observed change must represent a larger fragment, e.g., an enzyme or chemical reagent bound fragment.

In most cases it is necessary to hybridize a DNA sample containing a putative mutation with corresponding wild type. Since MIPC separates DNA fragments by base pair length, any reaction of the DNA sample with the enzyme or chemical reagent will produce a change in the retention time and/or the number of fragments in the MIPC chromatogram of the sample compared to the sample chromatogram prior to contact with the enzyme or chemical reagent. In the present invention, the enzymes and chemicals selectively react with a site of mutation, so that any change in the chromatogram indicates the presence of a mutation. If there is no change in the MIPC chromatogram after contacting the sample with the enzyme or chemical reagent, compared to the chromatogram produced prior to contacting the sample with an enzyme or chemical reagent, then the sample does not contain a mutation.

If needed, the separated fragments can be collected and their sequence verified by conventional techniques.

In one embodiment of the invention, a heteroduplex is formed by hybridizing a sample DNA fragment containing a putative mutation with its corresponding wild type fragment. When the mixture of sample and wild type is heated to about 95° C. the DNA duplexes denature to form single stranded polynucleotide fragments. Upon cooling slowly to about 50° or less, the single strands re-anneal to form a mixture of homoduplexes and heteroduplexes. The heteroduplex contains a heteroduplex mutation site, i.e., a site of base pair mismatch in a DNA duplex. The hybridization process is described in Example 1 and depicted schematically in FIG. 1.

In one embodiment of the present invention, if a DNA sample contains a mutation, an enzyme or chemical reagent which recognizes a mutation, cleaves the DNA strand at the mutation site, or within the vicinity of the mutation site, thereby creating a greater number of fragments each having fewer base pairs than were present in an original sample. Alternatively, if the enzyme or chemical reagent binds to a site of mutation without cleaving, then the resulting bound fragment will be larger than the original fragment, and the hydrophobicity may also be altered. MIPC is ideally suited to detect mutations which have been recognized by an enzyme or chemical reagent because MIPC separates DNA fragments on the basis of size and hydrophobic interactions.

An aliquot of the hybridized mixture is then analyzed using MIPC. Typically, such a chromatogram will show a single peak since all the fragments have the same base pair length. The hybridized sample is then contacted with an enzyme which recognizes base pair mismatches in a heteroduplex. Many enzymes are known in the art which can recognize one or more base pair variations, e.g., mismatches, in a heteroduplex. Non-limiting examples of enzymes which recognize a site of base pair mismatch in a heteroduplex include T4 endonuclease 7, T7 endonuclease 1, *E. coli* MutL protein, *E. coli* MutS protein, S1 nuclease, mung bean endonuclease, thymine glycosylase and cleavase enzyme. A thorough presentation of enzymes which can be used in are presented in the following references: Cotton, *Mutation Detection*, pp 67–95, Oxford University Press, (1997); Marshal, et al., *Genetics and Development* 6:275 (1996); Marshal, et al., *Nature Genetics* 6:177 (1995); Youil, et al., *Proc. Natl. Acad. Sci. USA* 92:87 (1995); U.S. Pat. No.

5,217,863 (1993) to Cotton; U.S. Pat. No. 5,698,400 (1997) to Cotton; U.S. Pat. No. 5,719,028 to Dahlberg (1998); Brow, et al., *Biomedical Products* p. 22, September, 1997. A comprehensive review of methods for detecting mutations has recently been published (*Laboratory Methods For The Detection Of Mutations and Polymorphisms in DNA*, ed. G. R. Taylor, CRC Press, 1997). These references and the references contained therein are incorporated in their entireties herein. Such enzymes cleave a DNA fragment at or near the mutation site thereby creating more fragments than were present in the original hybridized sample. Since the fragments so produced originate from the sample fragment, they are necessarily, smaller. Analysis of the DNA sample mixture by MIPC after contact with the enzyme will now show (n+1) peaks for each mutation site present in the sample, where "n" is the number of mutation sites in the original sample. Since the cleaved fragments are all smaller than original sample fragment, the peaks in the MIPC chromatogram will all have shorter retention times than the original sample fragment. In another embodiment of this aspect of the invention, MIPC can be performed at an elevated temperature in which all the strands are denatured (e.g., 65° C.), on aliquots of the reaction mixture obtained both before and after contact with the enzyme.

In general, any enzyme reported for cleavage of single-stranded DNA is a candidate for cleaving heteroduplexes in the vicinity of the mis-matched bases, D-loops, heteroduplexes formed between two strands of DNA which differ by a single base, an insertion or deletion.

S1 nuclease, a single strand specific nuclease, may be useful when multiple contiguous base changes or insertions/deletions are expected leading to heteroduplexes with extended regions of single stranded DNA. (Cotton, *Mutation Detection*, Oxford University Press, New York, p. 88 (1997).

In addition, to S1 nucleases, mung bean nucleases may also be used for the detection of mismatched bases in DNA heteroduplexes. Mung bean nucleases have been used to digest single stranded DNA at sites of mismatches. This method is highly dependent on sequence context (Shenk, et al., *Cold Spring Harb. Symp. Quant. Biol.* 1:61–67 (1975).

Bacteriophage resolvases may be useful reagents for rapid screening of DNA for mutations (Mashal, et al., *Nature Genetics* 9:177 (1995). Resolvases such as the T4 Endonuclease VII (T4E7) are able to cleave DNA which is in the form of a Holliday structure formed after recombination events (Youil, et al., *Proc. Natl. Acad. Sci. USA* 92:87 (1995)). They also cleave all single base pair mismatches between 10% and 50% efficiency. For example, PCR amplified DNA fragments from normal and mutated DYS271 sequences are mixed, denatured, and annealed to generate mismatches for cleavage by the T4E7 as described in Examples 2 and 4. Resolvases will cleave from one to four of the strands in the two heteroduplexes. Even if only one of the four potential sites is cleaved, this is sufficient to detect the presence of the mutation (Cotton, *Mutation Detection*, Oxford University Press, New York, p. 91–93 (1997)).

Mismatch repair enzymes may also be used to identify DNA base changes. The nature and site of a mutation can be determined form the size of the cleaved DNA fragment (*Laboratory Methods for the Detection of Mutations and Polymorphisms in DNA*, G. R. Taylor (ed), CRC Press, New York, pp. 195–205 (1997)) These enzymes nick one strand at the site of the mismatch. Upon denaturation, one strand is cleaved.

Ligases join two fragments of DNA together end to end. A nick in duplex DNA may be sealed by joining the 3' and 5' ends on either side of the nick. The requirement for matched base pairs surrounding the nick can be used to show the presence of a mismatch by failure to seal the nick. The nick can be formed by annealing an oligonucleotide with the 3' end over the site of interest, to another oligonucleotide annealed adjacently (Pritchard, et al., *Nucleic Acids Research* 25:3403 (1997)).

In addition to the enzymes above for which heteroduplex DNA is the substrate, the sequence specific endonucleases will give rise to fragment length polymorphism in homoduplexes if the mutation is sited with the sequence recognition motif. The fragment length polymorphism can be detected using DMIPC.

In another embodiment of the invention, a mutation in a DNA fragment is detected by MIPC using a restriction enzyme. A restriction enzyme recognizes a specific nucleotide sequence in DNA and cleaves the DNA double strand at, or near one end of the recognized sequence. If a mutation is present in the sample, the restriction enzyme will not cleave the DNA strand since, by definition, a mutation has a different nucleotide sequence than a wild type fragment and the mutation will not be recognized by the restriction enzyme. Thus, a MIPC chromatogram of the sample will produce a single peak prior to treatment with a restriction enzyme. If a mutation is not present in the sample, a MIPC chromatogram will produce more than one peak, since the restriction enzyme will recognize the nucleotide sequence it recognizes and will cleave the DNA fragment at or near such sequence locations. If a mutation is present, an MIPC chromatogram will produce fewer peaks than wild type, after the sample is contacted with a restriction enzyme since no cleavage will occur at the mutation site. An advantage of this embodiment is that a mutation can be detected in both a heteroduplex and in a heterozygous homoduplex.

In a related embodiment, a restriction enzyme can be used to cleave a DNA fragment containing a mutation while leaving the corresponding wild type intact. In this embodiment, a restriction enzyme is selected which is known to recognize the base sequence in the mutant fragment but not in the wild type fragment. Hence, a sample containing a putative mutation relative to wild type is contacted with a restriction enzyme which recognizes the base pair sequence of the mutation only. MIPC analysis of wild type or sample, prior to contact with enzyme will produce a chromatogram showing a single peak. MIPC analysis of the sample after contact with enzyme will produce a chromatogram showing one peak if the sample does not contain a mutation. MIPC analysis of the sample, after contact with enzyme, will produce a chromatogram showing (n+1) peaks if the sample contains a mutation since cleavage will occur at or near each mutation site recognized by the enzyme. Such an approach has been described by Mullis (U.S. Pat. No. 4,683,202 (1987)) wherein Hinfl restriction enzyme, which recognizes the mutant sequence in the sickle cell gene, was used to demonstrate the presence of the sickle cell mutation in a clinical sample. In that case, the sample and wild type were treated with Hinfl and analyzed by gel electrophoresis. An autoradiograph of the gel showed a single band in the wild type lane but two bands in the sample lane, indicating the presence of a mutation in the sample. It is an important aspect of the present invention that the analysis can be greatly simplified, relative to electrophoresis, by using MIPC to separate and detect the relevant DNA fragments. The Mullis reference and the references contained therein are incorporated in their entireties herein.

In a further embodiment, a mutation can be detected using MIPC in a hybridized mixture containing a DNA heteroduplex which has been contacted with an enzyme that "nicks" a heteroduplex at or near the mutation site. The term "nick" refers to enzymatic cleavage of only one strand of a heteroduplex at or near the mutation site, while leaving the other strand intact. Examples include T4 endonuclease 7 or T7 endonuclease 1 within short exposure times, MutY, and thymine glycosylase. In this embodiment, an aliquot of a hybridized mixture of DNA fragments is analyzed by MIPC. The chromatogram obtained from this analysis shows a single peak since all the fragments have the same base pair length. Another aliquot of the mixture is contacted with a nicking enzyme. Applicants have surprisingly discovered that nicked double stranded DNA fragments have shorter retention times relative to the un-nicked DNA. If the mixture contains a mutation, (n+1) peaks will be seen in the MIPC chromatogram, each peak having a shorter retention time than the untreated sample and wherein, n equals the number of base pair mismatches in the heteroduplex. If the sample mixture does not contain a mutation, then a single peak will be seen in the MIPC chromatogram. This peak will have the same retention time as the peak produced by the untreated sample. In another embodiment of this aspect of the invention, MIPC can be performed on an aliquot of the reaction mixture at an elevated temperature in which all the strands are denatured (e.g., 65° C.), both before and after contact with the enzyme.

Figure 2:
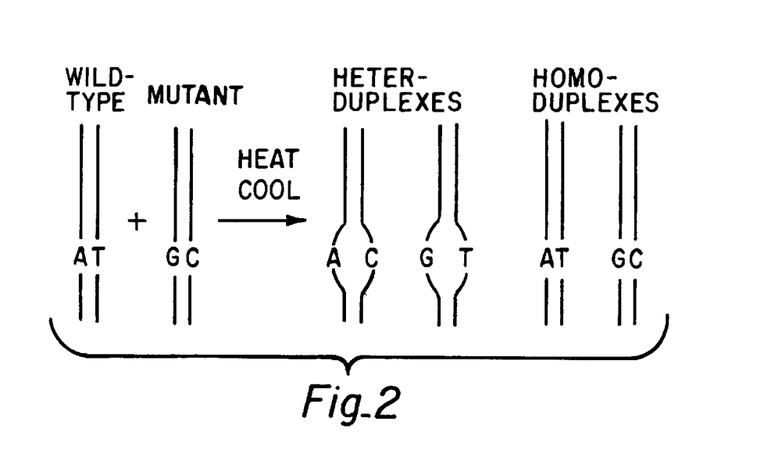
FIG. 2 is a schematic representation of hybridization of wild type DNA strand with homozygous mutant strand showing the production of two homoduplexes and two heteroduplexes.

In still another embodiment of the invention, a mutation can be detected by MIPC when an enzyme which is capable of detecting mutations binds to, or complexes with, the DNA fragment at or near a mutation site without cleaving. Non-limiting examples of such enzymes include RNAse A, and mismatch repair enzymes such as MutY, MutS, MutL, MutH and thymine glycosylase. Sequence recognition enzymes are discussed in U.S. Pat. No. 5,459,039 to Modrich (1995). This reference and the references contained therein are incorporated in their entireties herein. In this embodiment, a DNA sample is hybridized with wild type to produce a mixture of homoduplexes and heteroduplexes if a mutation is present, or an unchanged homoduplex if a mutation is not present. A DNA sample will produce one peak when analyzed by MIPC prior to contact with the mutation binding enzyme. If a mutation is not present in the sample, the MIPC chromatogram will show no change after contact with the enzyme. If a mutation is present in the sample, the MIPC chromatogram will show a peak shifted, e.g. to a longer retention time, compared to a sample which has not been contacted with the enzyme. This longer retention time peak represents the enzyme bound mutation containing fragment. FIG. 2 shows a MIPC chromatogram of a sample prior to contact with an enzyme and a chromatogram showing the peak shifted to longer retention time of an enzyme bound DNA fragment. Although an enzyme which binds to a mutation binding site may cleave the DNA strand after a certain length of time, it is still possible to detect the bound form of DNA/enzyme complex if the MIPC analysis is performed at an early time, e.g., within 2 to 10 minutes of contacting the sample with the enzyme. Preferably, the MIPC analysis is performed within 5, and optimally within 2 minutes of contacting the sample with the enzyme.

In another embodiment of the present invention, the mutation site binding enzymes of the present invention can be inactivated and stabilized in the bound complex with the DNA using a conventional cross-linking agent such as formaldehyde (Orlando, et al. Cell 75:1187 (1993)).

It will also be appreciated that enzymes which cleave at a site of mutation can be modified by known methods to a provide an inactive enzyme which can no longer cleave, but which retains its ability to bind. The use of such modified enzymes can also be used in the method of the present invention, and are exemplified by T4 endonuclease VII (T4E7) modified by site-directed mutagenesis, as described by Giraud-Panis, et al. (*J. Biol. Chem.* 271:33148 (1996)).

The present invention further relates, in part, to forms of mispair recognition proteins which have been altered to provide an inherent means for modifying at least one strand of the DNA duplex in the vicinity of the bound mispair recognition protein. In a principal embodiment of this aspect of this invention, the altered mispair recognition protein is the modified product of the mutS gene of *E. coli* or is another functionally homologous modified protein to which is attached an hydroxyl radical cleaving function; and the DNA modification step in the DNA mispair localization method further comprises contacting this modified protein with the DNA under conditions such that the radical cleaving function cleaves at least one strand of the DNA in the vicinity of the protein. Methods for attaching an hydroxyl radical leaving function to a DNA binding protein are known in the art are reviewed in U.S. Pat. No. 5,459,039 to Modrich (1995).

It has been reported that enzymes such as T4E7 can cause non-specific cleavage of DNA (Youil, et al., *Proc. Natl. Acad. Sci.* 92:87 (1995)). Such non-specific cleavage can create ambiguity in the analysis of a sample containing a putative mutation. In a preferred embodiment of the invention, therefore, a sample is analyzed after contact with an enzyme using MIPC at various time intervals. Such intervals can be 0, 2, 5, 7, 10, 15, 20, 25, 30, 40, 50, and 60 minutes. Since non-specific cleavage is generally much slower than specific cleavage, an analysis time can be determined at which the ratio of specific to non-specific cleavage is at a maximum. The sampling time so determined can then be used in subsequent screening.

The evaluation of specific to non-specific cleavage is possible using MIPC because of the detection sensitivity of the method and because the analysis time per sample is only about 5 minutes. Such an analysis is not possible, in the practical sense, using gel based analytical methods, because of their relatively low sensitivity and long analysis time (several hours). As discovered by Applicants, a major advantage of using MIPC is that the greater sensitivity of the method allows one to observe any cleavage products in the sample after minimum contact with enzyme. In a preferred embodiment, as illustrated in Example 5, any change in a MIPC chromatogram can be analyzed within minutes of contact with enzyme, and a time-course of the ratio of specific to non-specific cleavage can be obtained. This method minimizes the ambiguity in the analysis related to non-specific cleavage.

In a related embodiment of the invention, MIPC can be used to detect mutations in DNA following treatment of a DNA strand which contains a putative mutation with a non-proteinaceous chemical reagent which recognizes variations in nucleotide sequence relative to wild type. Chemical reagents are known in the art which bind to duplex DNA at an intercalation site at or near a mutation site in a heteroduplex. Non limiting examples of such compounds include bis(2,2'-bipyridyl)chrysenequinone diimine rhodium(III), bis(2,2'-bipyridyl)chrysenequinone diimine rhodium(III), (2,2'-bipyridyl)-bis(phenanthrenequinone) diimine rhodium (III), (bis(phenanthroline)dipyridophenazine ruthenium(II), bis(phenanthroline)dipyridophenazine ruthenium(III). The syntheses and mutation detection properties of site selective organometallic intercalators is described by Barton, et al. in the following references: *J. Am Chem. Soc.* 119:12986

(1997); *J. Am. Chem. Soc.* 119:2921 (1997); *Inorg. Chem.* 37:29 (1998). These references and the references therein are herein incorporated in their entireties.

One such a compound is bis(2,2'-bipyridyl) chrysenequinone diimine rhodium(III). The synthesis and mutation detection properties of this compound are described by Jackson, et al. (*J. Am. Chem. Soc.* 119:12986 (1997). This reference and the references contained therein are incorporated in their entireties herein. It is thought that site selective, non-covalent intercalation occurs because of helix destabilization caused by base pair mismatch in a heteroduplex. Mismatch recognition seems to be broadly correlated with the degree of helix destabilization caused by the mismatch which allows the bulky chrysene intercalator to bind. Photocleavage can be effected by irradiating the intercalated complex at 365 nm with a mercury/xenon arc lamp. Jackson and Barton have found that chrysene-rhodium(III) intercalator recognizes CC, CA, TT, TA, AA, and TC mismatches as evidenced by cleavage at or near these sites upon irradiation of the DNA chrysene-rhodium(III) complex at 365 nm.

In an additional embodiment of this invention, MIPC can be used to detect mutations which are recognized by chemical site recognition intercalating agents containing rhodium or ruthenium. A non-limiting example of such an intercalator is bis(2,2'-bipyridyl) chrysenequinone rhodium(III). In this embodiment, a DNA fragment containing a putative mutation is hybridized. MIPC analysis of the hybridized sample will produce a chromatogram showing a single peak since all the fragments in the hybridized sample have the same base pair length. The hybridized sample is then contacted with a site recognition intercalating agent such as bis(2,2'-bipyridyl) chrysenequinone rhodium(III). MIPC analysis will produce a chromatogram showing a single peak if no mutation is present in the sample. If a mutation is present, the chromatogram will show a peak having a different retention time compared to wild type. Alternatively, the sample contacted with bis(2,2'-bipyridyl) chrysenequinone rhodium(III) can be irradiated at 365 nm. If the sample does not contain a mutation, there will be no change in the chromatogram compared to wild type. If the sample contains a mutation, the chromatogram will show (n+1) peaks, since cleavage will occur at each mutation site present in the sample.

An important aspect of the invention, surprisingly discovered by the Applicants, is that samples which have been treated with sequence recognition organometallic intercalators can be analyzed directly by MIPC or DMIPC. It is not necessary to remove any endogenous reagents or by-products prior to analysis. This is unusual, since such endogenous material, organometallic compounds, usually interfere in HPLC separations. This discovery makes possible the unattended, automated analysis of multiple samples in mutation detection screening assays.

The discussion herein above has focussed on the use of MIPC to separate and detect DNA fragments produced by chemical reagents and enzymes when a mutation is present in a sample. It is also possible to detect mutations in the identical manner described herein using other forms of chromatography which are capable of effecting the necessary separations of DNA fragments produced by sequence recognition enzymes or chemical reagents. Accordingly, in related embodiments of the invention, a DNA fragment can be contacted with each and any of the chemical and enzymatic mutation site binding reagents described hereinabove. Analysis of the sample before and after contact with mutation detection agents is then performed using size exclusion chromatography, ion exchange chromatography on porous separation media, ion exchange chromatography on non-porous separation media, and reverse phase chromatography. These chromatography methods have been used to separate DNA fragments as described Hirabayashi, et al., (*Anal. Biochem.* 178:336 (1989), Ohimya, et al., (ibid., 189:126 (1990), Kato, et al., *J. Chromatog.*, 168:264 (1989), and Westman, et al., (ibid., 166:158 (1987)). These references and the references contained therein are incorporated in their entireties herein. The use of chromatographic analytical methods to detect mutations has not been previously reported.

In each of the enzymatic and chemical mutation recognition scenarios described herein above, analysis for the presence or absence of mutations was previously performed by gel electrophoresis, denaturing gel electrophoresis, or the corresponding capillary electrophoresis techniques. The serious disadvantages of these analytical techniques have been discussed above (*Laboratory Methods For The Detection Of Mutations and Polymorphisms in DNA*, ed. G. R. Taylor, CRC Press, 1997). Chromatographic methods in general and MIPC, in particular, greatly simplify the analysis and improve accuracy, reproducibility, sensitivity, data collection and storage, and throughput. The use of MIPC to detect mutations which have been recognized by enzymes or chemical agents has not been previously reported and provides an major improvement in the mutation detection art.

It will be apparent that the types of enzymes and the conditions for MIPC analysis can be varied to perform mutation detection by the methods of the present invention. Certain enzymes are known to bind, but not cleave, at a mutation site to form a dsDNA-enzyme complex which can be separated form unbound dsDNA by MIPC under non-denaturing conditions. Other enzymes bind and then cleave. Both the bound enzyme and the cleaved DNA products can be observed using MIPC. The MIPC separation can be performed at an elevated "enzyme releasing temperature" at which the enzyme is released from the DNA-enzyme complex, but the DNA remains as a duplex. Alternatively, the products of the enzyme cleavage can be analyzed at an elevated temperature so that all of the DNA products are denatured during the MIPC separation. Non-proteinaceous chemical intercalators, as described herein, can bind to a dsDNA at a mutation site without cleavage to form a DNA-intercalator complex which can be separated from unbound DNA by MIPC under non-denaturing conditions. In some cases, bound intercalators can be light-activated to cleave the DNA in the vicinity of the mutation site. The products can be analyzed using MIPC under non-denaturing conditions or denaturing conditions.

In summary, under non-denaturing conditions of MIPC separation, DNA species which are the result of nicking or cleaving are identified by a change in the number of peaks in the chromatogram or altered retention times. Complexes between DNA and intercalators or DNA and proteins also show altered retention times under non-denaturing conditions.

MIPC also offers the capability of separating under progressively more denaturing conditions using increased temperature as a preferred denaturing agent. Other conditions such as elevated pH, urea, formamide, or counterion can also be used. Under fully denaturing conditions, dissociation of mismatch binding proteins and mismatch cleaving enzymes from binding sites on DNA will occur. Dissociation of duplex DNA under denaturing conditions leads to the release of nicked strands, previously annealed to a complementary strand, to generate three or more independent single-stranded species which can be resolved into three or more peaks by MIPC.

Other features of the invention will become apparent in the course of the following descriptions of exemplary embodiments which are given for illustration of the invention and are not intended to be limiting thereof.

Procedures described in the past tense in the examples below have been carried out in the laboratory. Procedures described in the present tense have not yet been carried out in the laboratory, and are constructively reduced to practice with the filing of this application.

EXAMPLE 1

Separation Of An Enzyme Bound DNA Fragment

Samples for PCR amplification were purchased from Perkin-Elmer Applied Biosystems (Foster City, Calif.) in the GeneAmp® (PCR Reagent Kit (Part No. N801-0055), which included AmpliTaq® DNA polymerase, GeneAmp, 10x PCR Buffer, dNTP's as well as DNA template and primers. The DNA template was diluted to 100 ng/mL in 10 mM Tris-HCl, pH 8.0 (Cat. No. 0291, Teknova, Half Moon Bay, Calif., USA), 1 mM EDTA, pH 8.0 (Cat. No. 0306, Teknova), 10 mM NaCl (Cat. No. S7653, Sigma, St. Louis, Mo., USA). A 500-bp product was amplified from the DNA control template (bacteriophage Lambda DNA) from Control Primer #1 (5'-GATGAGTTCGTGTCCCTACAACTGG-3') and Control Primer #2 (5'-GGTTATCGAAATCAGCCACAGCGCC-3').

Components were added to PCR tubes (Part No. TFI-0201, MJ Research, Watertown, Mass., USA) in the following order: 53 µL ddH20, 10 µL 10x PCR buffer, 200 µM each dNTP, 2.5U/100 µL AmpliTaq®, 1 µM Control Primer #1, 1 µM Control Primer #2, and 1 ng DNA control template to total 100 µL. Amplification was performed on the MJ Research (Watertown, Mass., USA) PTC-100 Thermocycler using 15 or 35 PCR cycles.

One part HaeIII restriction enzyme (Sigma-Aldrich Corp., St. Louis, Mo., Cat. No. R5628) was diluted with 30 parts of double distilled water. One part of the diluted enzyme was added to two parts of the PCR product. The 500 bp PCR product has four cleavage sites for HaeIII at bases 37, 47, 452, and 457. An aliquot of the PCR product containing the 500 bp DNA fragment, prior to contact with the enzyme, was applied to an MIPC column at 50° C. and eluted with Solvent A (0.1M triethylammonium acetate(TEAA)) and Solvent B (0.1M TEAA in 25% acetonitrile) using the following gradient: comprising A and B:

| TIME (min) | % B |
|---|---|
| 0–3 | 35–55 |
| 3–7 | 55–65 |
| 7–9.5 | 65 |
| 9.5–11 | 100 |
| 11–13 | 35 |

The flow rate was 0.75 mL/min. A UV detector operating at 260 nm was used to detect the DNA fragments.

Figure 1:
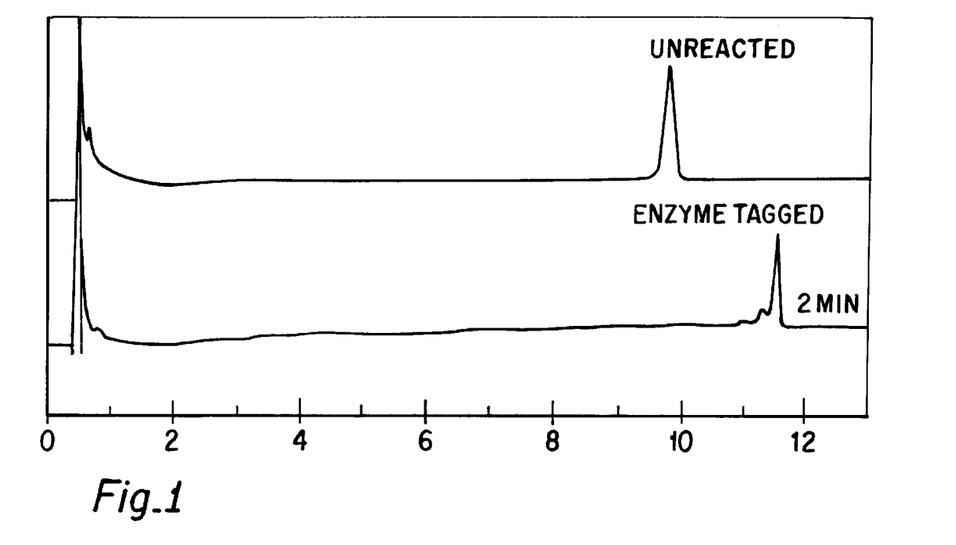
FIG. 1 is a MIPC chromatogram of a DNA fragment containing a mutation, prior to contact with HaeIII enzyme (top profile). The bottom profile is a MIPC chromatogram of a DNA fragment containing a mutation bound to HaeIII enzyme after 2 minutes contact with enzyme.

The MIPC chromatogram of the untreated 500 bp sample, seen in the upper half of FIG. 1, showed a single peak having a retention time of about 9 minutes.

The lower half of FIG. 1 shows the MIPC chromatogram of the 500 bp sample after 2 minutes of contact with the HaeIII enzyme. Elution conditions were identical to those described above. A single main peak having a retention time of about 11 minutes was seen. The observed shift to longer retention time is indicative of the enzyme bound sample.

EXAMPLE 2

Analyte Hybridization Procedure and MIPC Analysis

A DYS271 209 bp mutation standard containing a mixture of the homozygous mutant DNA fragment (with an A to G mutation at position 168) combined with the corresponding wild type fragment in an approximately 1:1 ratio (the mixture is available as a Mutation Standard from Transgenomic, Inc., San Jose, Calif.; the mutation is described by Seielstad et al., Hum. Mol. Genet. 3:2159 (1994)) was heated at 95° C. for 3–5 minutes then cooled to 25° C. over 45 minutes. A mixture of two homoduplexes and two heteroduplexes was produced in the hybridization process, as shown schematically in FIG. 2.

The hybridized sample (138 ng DNA) was injected onto an MIPC column (50 mm×4.6 mm i.d.) DNASep™ (Transgenomic, Inc. San Jose, Calif.) at 52° C. The chromatography performed using a WAVE™ DNA Fragment Analysis System (Transgenomic, Inc.) was monitored at 260 nm using an UV detector. The column was eluted at 0.75 mL/min with a solvent A: 0.1M TEAA and solvent B: 0.1M TEAA, 25% acetonitrile using the following gradient:

| Time (min) | % A | % B |
|---|---|---|
| 0.0 | 65.0 | 35.0 |
| 3.0 | 45.0 | 55.0 |
| 10.0 | 35.0 | 65.0 |
| 13 | 35.0 | 65.0 |
| 14.5 | 0.0 | 100.0 |
| 16.5 | 65.0 | 35.0 |
| 18.5 | 65.0 | 35.0 |

EXAMPLE 3

Mutation Detection Using a Rhodium Intercalator and Analysis by MIPC

Bis(2,2'-Bipyridyl)chrysenequinone diimine rhodium(III) is synthesized as described by Jackson and Barton (J. Am. Chem. Soc. 119:12986 (1997)).

The DNA template, bacteriophage Lambda (base pairs 31500-32500) with a mutation at position 32061 (available from FMC Corp. BioProducts, Rockland, Me.), is amplified by means of PCR. The Lambda sequence has been published by O'Conner et al. in Biophys. J74:A285 (1998) and by FMC Corp. at the Mutation Detection 97 4th International Workshop, Human Genome Organization, May 29–June 2, 1997, Brno, Czech Republic, Poster no. 29.

The PCR conditions used with each of the primers are described in the table below. All the components are combined and vortexed to ensure good mixing, and centrifuged. Aliquots are then distributed into PCR tubes as shown in the following table:

| COMPONENT | VOLUME |
|---|---|
| Pfu 10X Buffer (Cat. No. 600153-82, Stratagene, Inc., La Jolla, CA) | 5 µL |
| 100 µM dNTP Mix | 4 µL |
| Primer 1 (forward) | 7.5 µL |
| Primer 2 (reverse) | 8.5 µL |

-continued

| COMPONENT | VOLUME |
|---|---|
| H$_2$O | 19.5 µL |
| Lambda DNA Template | 5 µL |
| PFUTurbo™ (600250, Stratagene) | 0.5 µL |

The PCR tubes are placed into a thermocycler and the temperature cycling program was initiated. The cycling program parameters are shown in the table below:

| STEP | TEMPERATURE | TIME |
|---|---|---|
| 1 | 94° C. | 2 minutes |
| 2 | 94° C. | 1 minute |
| 3 | 58° C. | 1 minute |
| 4 | 72° C. | 1 minute |
| 5 | Go to Step 2, 34X | |
| 6 | 72° C. | 10 minutes |
| 7 | End | |

The MIPC conditions used for the separation at 50° C. is shown below: Eluent A: 0.1M TEAA; Eluent B: 0.1M TEAA, 25% Acetonitrile; Flow rate: 0.900 mL/min; Gradient:

| Time (min) | % A | % B |
|---|---|---|
| 0.0 | 50.0 | 50.0 |
| 0.1 | 45.0 | 55.0 |
| 4.6 | 36.0 | 64.0 |
| 4.7 | 0.0 | 100.0 |
| 5.2 | 0.0 | 100.0 |
| 5.3 | 50.0 | 50.0 |
| 7.8 | 50.0 | 50.0 |

The 100 bp Lambda fragment sequence (base positions 32011–32110) has an A to C mutation at position 51 corresponding to position 32061 in Lambda. The cart below lists the primers used:

| Primers |
|---|
| Forward Primer: |
| 5'-GGATAATGTCCGGTGTCATG-3' |
| Reverse Primer: |
| 3'-GGACACAGTCAAGACTGCTA-5' |

An aliquot of hybridized Lambda DNA sample is analyzed using MIPC. The chromatogram shows a single peak at about 4.8 min.

Another aliquot of the hybridized DNA sample (10 µM) is combined with 1 µM bis(2,2'-bipyridyl)chrysenequinone diimine rhodium(III) in 50 mM Tris, 20 mM sodium acetate, 18 mM sodium chloride at pH7. The reaction is stirred for 11 minutes, then irradiated for 13 minutes at 365 nm with an Oriel mercury/xenon arc lamp. Analysis of this reaction mixture using MIPC shows two peaks, each having a shorter retention time than the untreated sample peak. This result indicates the presence of a pair mismatch in the sample.

EXAMPLE 4

Mutation Detection Using T4 Endonuclease VII (T4E7) and Analysis by MIPC

An aliquot of a hybridized DNA DYS271 209 bp mutation standard (with an A to G mutation at position 168), was prepared and analyzed by MIPC as described in Example 2. The chromatogram showed a single peak at about 7.5 minutes.

Figure 3:
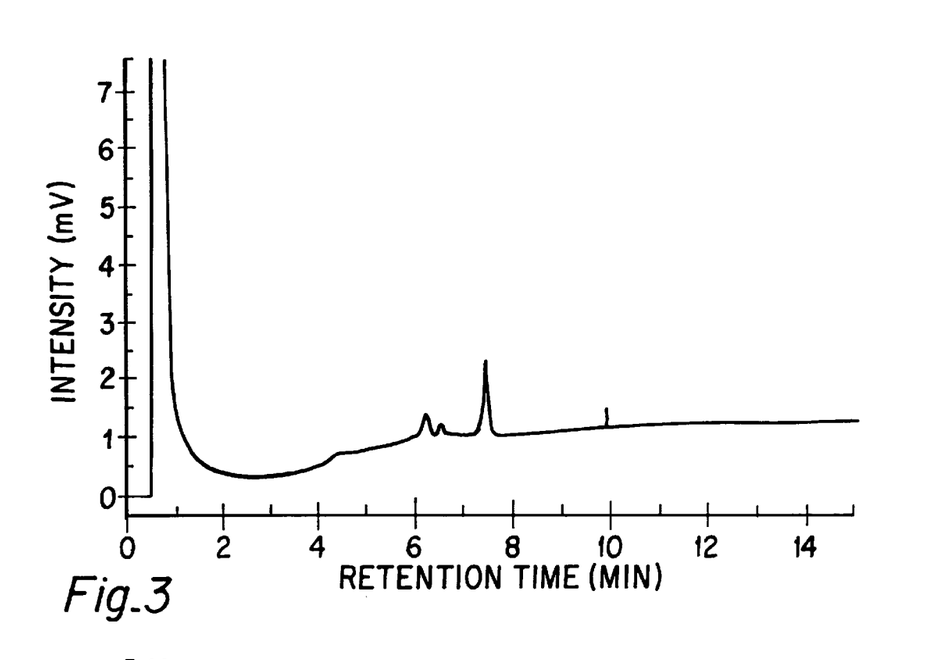
FIG. 3 is a MIPC chromatogram of a DYS271 209 base pair mutation standard after 25 minutes reaction with T4EVII endonuclease
Figure 4:
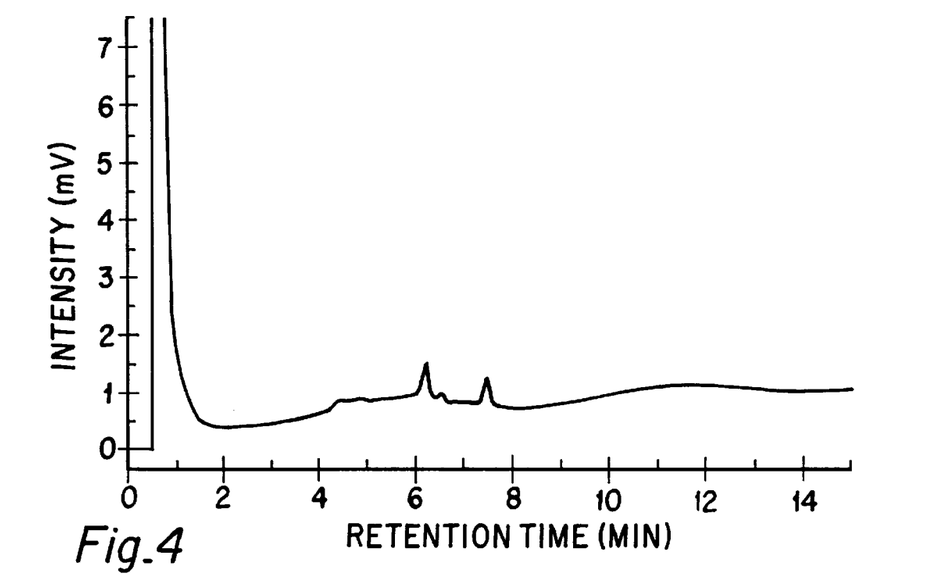
FIG. 4 is a MIPC chromatogram of a DYS271 209 base pair mutation standard after 65 minutes meaction with T4EVII endonuclease

To a 10 µL aliquot of the hybridized sample (0.01 µg/µL was added to a mixture comprising 3 µL Tris-EDTA buffer, 2 µL (500U/µL) T4E7 enzyme. The total reaction volume was about 15 µL. The reaction was incubated at 37° C. for 65 minutes. The reaction mixture was then analyzed by MIPC as described in Example 2 after 25 minutes and again after 65 minutes. The MIPC chromatogram after 25 minutes (FIG. 3) of reaction showed a peak about 6.25 minutes which represents the expected 168 bp fragment. The MIPC chromatogram after 65 minutes (FIG. 4) of reaction showed an increase in the size of the 168 bp fragment peak at 6.25 minutes. This result indicates the presence a single mutation site in the sample.

The MIPC analysis was performed at 52° C. at a flow rate of 0.75 mL/min. UV detection was at 260 nm. The column was eluted with a gradient comprising solvent A (0.1M TEAA) and solvent B (25% acetonitrile in 0.1M TEAA) as described in Example 2.

An identical procedure was applied to a different hybridized DNA sample. The MIPC chromatogram showed a single peak, matching the retention time of the untreated sample. This result indicates that the sample does not contain a mutation.

EXAMPLE 5

MIPC Determination of an Optimum Ratio of Specific to Non-specific Cleavage Mediated by T4 Endonuclease VII (T4E7)

A heteroduplex DNA sample is treated with T4E7 exactly as described in Example 4 above, except that the reaction is allowed to proceed for 60 minutes. Aliquots of the reaction are removed and analyzed using MIPC after 0, 2, 5, 7, 10, 15, 20, 25, 30, 40, 50, and 60 minutes. The ratio of peaks due to specific cleavage to non-specific cleavage is determined by integration of the peaks in the chromatogram using standard computer software. The reaction time corresponding to the maximum ratio so determined is noted and used to analyze subsequent sample reactions in screening assays or for any chosen purpose.

While the foregoing has presented specific embodiments of the present invention, it is to be understood that these embodiments have been presented by way of example only. It is expected that others will perceive and practice variations which, though differing from the foregoing, do not depart from the spirit and scope of the invention as described and claimed herein.

The invention claimed is:

1. A method for analyzing a sample of double stranded DNA to determine the presence of a mutation site therein comprising:
   a) contacting said sample with a mutation site binding reagent which binds within the vicinity of said mutation site, and
   b) chromatographically separating and detecting the product of step (a) while the mutation site binding reagent remains bound to the mutation site.

2. A method of claim 1, further comprising comparing the separated product of step (b) to a standard.

3. A method of claim 1 wherein step (b) comprises analysis by Matched Ion Polynucleotide Chromatography, size exclusion chromatography, ion exchange chromatography, or reverse phase chromatography.

4. A method of claim 1 wherein step (b) comprises analysis by Matched Ion Polynucleotide Chromatography.

5. A method of claim 4 where in said mutation site binding reagent is a protein reagent which binds within the vicinity of said mutation site and remains bound during the analysis of step (b).

6. A method of claim 1 comprising hybridizing the DNA sample with corresponding wild type DNA prior to step (a).

7. A method of claim 1 wherein said mutation site binding reagent is a protein reagent which binds within the vicinity of said mutation site.

8. A method of claim 7 wherein said protein reagent is selected from the group consisting of endonucleases, restriction enzymes, ribonucleases, mismatch repair enzymes, resolvases, helicases, cleavases, and ligases.

9. The method of claim 7 wherein said protein reagent has been modified by site specific mutagenesis.

10. A method of claim 1 wherein said mutation site binding reagent is a protein reagent.

11. A method of claim 10 wherein said protein reagent is selected from the group consisting of endonucleases, restriction enzymes, ribonucleases, mismatch repair enzymes, resolvases, helicases, cleavases, and ligases.

12. A method of claim 10, wherein the enzyme is selected from the group consisting of T4 endonuclease 7, T7 endonuclease 1, S1 nuclease, mung bean endonuclease, MutY protein, MutS protein, MutH protein, MutL protein, cleavase, and HINF1.

13. A method of claim 1 wherein said mutation site binding reagent is a non-proteinaceous chemical reagent.

14. A method of claim 13 wherein said chemical reagent binds within the vicinity of said mutation.

15. A method of claim 13 wherein said chemical reagent is a DNA intercalator.

16. A method of claim 13 wherein said chemical reagent is an organometallic reagent.

17. A method of claim 16 wherein said intercalator contains rhodium or ruthenium.

18. A method of claim 16 wherein said intercalator is selected from the group consisting of bis(2,2'-bipyridyl) chrysenequinone diimine rhodium(III), bis(2,2'-bipyridyl) chrysenequinone diimine rhodium(III), (2,2'-bipyridyl)-bis (phenanthrenequinone) diimine rhodium(III), (bis(phenanthroline)dipyridophenazine ruthenium(II), and bis(phenanthroline)dipyridophenazine ruthenium(III).

19. A chromatographic method for analyzing a DNA sample to determine the presence of mutations in said sample, the method comprising:

(a) separating said sample using a chromatographic method which produces a first chromatogram comprising peaks or other shapes which represent separated components of the sample;

(b) contacting said sample with a mutation site binding reagent which binds within the vicinity of said mutation site;

(c) separating the product of step (b) by the chromatographic method of step (a) to produce a second chromatogram while the mutation site binding reagent remains bound to the mutation site; and (d) comparing the chromatogram of step (c) to the chromatogram of step (a), wherein a change in the retention time or the number of peaks or other shapes in the chromatogram of step (c) indicates the presence of a mutation in said sample.

20. A method of claim 19, wherein the chromatographic method is Matched Ion Polynucleotide Chromatography.

21. A method of claim 19, wherein the chromatographic method is selected from the group consisting of Matched Ion Polynucleotide Chromatography, size exclusion chromatography, ion exchange chromatography, and reverse phase chromatography.

22. A method of claim 19, wherein the DNA sample is hybridized with corresponding wild type.

23. A method of claim 19, wherein the mutation site binding reagent is an enzyme.

24. A method of claim 19, wherein the mutation site binding reagent a non-proteinaceous chemical reagent.

25. A method of claim 23, wherein the enzyme binds at or near a site of base pair mismatch.

26. A method of claim 23, wherein the enzyme is selected from the group consisting of endonucleases, restriction enzymes, ribonucleases, mismatch repair enzymes, resolvases, helicases, and ligases.

27. A method of claim 23, wherein the enzyme is selected from the group consisting of T4 endonuclease 7, T7 endonuclease 1, S1 nuclease, mung bean endonuclease, MutY protein, MutS protein, MutH protein, MutL protein, cleavase, and HINF1.

28. A method of claim 24 wherein the chemical reagent cleaves a DNA duplex at or near a site of base pair mismatch.

29. A method of claim 24, wherein the chemical reagent binds at or near a site of base pair mismatch.

30. A method of claim 24, wherein the chemical reagent is a DNA intercalator which contains rhodium or ruthenium.

31. A method of claim 30, wherein the intercalator is selected from the group consisting of bis(2,2'-bipyridyl) chrysenequinone diimine rhodium(III), bis(2,2'-bipyridyl) chrysenequinone diimine rhodium(III), (2,2'-bipyridyl)-bis (phenanthrenequinone) diimine rhodium(III), (bis(phenanthroline)dipyridophenazine ruthenium(II), and bis(phenanthroline)dipyridophenazine ruthenium(III).

* * * * *